(12) United States Patent
Alisi et al.

(10) Patent No.: US 9,249,097 B2
(45) Date of Patent: Feb. 2, 2016

(54) 3-AMINOCARBAZOLE COMPOUND, PHARMACEUTICAL COMPOSITION CONTAINING IT AND PREPARATION METHOD THEREFOR

(71) Applicant: AZIENDE CHIM. RIUN. ANG. FRANC. A.C.R.A.F. S.p.A., Rome (IT)

(72) Inventors: Maria Alessandra Alisi, Rome (IT); Nicola Cazzolla, Albano Laziale (IT); Isabella Coletta, Rome (IT); Patrizia Dragone, Rome (IT); Guido Furlotti, Rome (IT); Barbara Garofalo, Rome (IT); Angelo Guglielmotti, Rome (IT); Giorgina Mangano, Rome (IT); Caterina Maugeri, Rome (IT)

(73) Assignee: AZIENDE CHIMICHE RIUNITE ANGELINI FRANCESCO A.C.R.A.F. S.p.A., Rome (IT)

( * ) Notice: Subject to any disclaimer, the term of this patent is extended or adjusted under 35 U.S.C. 154(b) by 0 days.

(21) Appl. No.: 14/109,259

(22) Filed: Dec. 17, 2013

(65) Prior Publication Data
US 2014/0107174 A1    Apr. 17, 2014

Related U.S. Application Data

(63) Continuation of application No. 12/991,815, filed as application No. PCT/EP2009/055652 on May 11, 2009, now Pat. No. 8,637,682.

(30) Foreign Application Priority Data

May 14, 2008    (EP) .................................. 08425336

(51) Int. Cl.
*C07D 209/88* (2006.01)
(52) U.S. Cl.
CPC .................................. *C07D 209/88* (2013.01)
(58) Field of Classification Search
CPC .................................................. C07D 209/88
See application file for complete search history.

(56) References Cited

U.S. PATENT DOCUMENTS

| | | | |
|---|---|---|---|
| 6,399,631 | B1 | 6/2002 | Elliott et al. |
| 7,879,900 | B2 | 2/2011 | Alisi et al. |
| 8,207,214 | B2 | 6/2012 | Alisi et al. |
| 2008/0207727 | A1 | 8/2008 | Alisi et al. |
| 2008/0287518 | A1 | 11/2008 | Polenzani et al. |

FOREIGN PATENT DOCUMENTS

| | | |
|---|---|---|
| WO | 01 07409 | 2/2001 |
| WO | 02 051806 | 7/2002 |
| WO | 02 096902 | 12/2002 |
| WO | 2006 122680 | 11/2006 |
| WO | 2007 014687 | 2/2007 |

OTHER PUBLICATIONS

Inoue, Hiroyasu et al., "Feedback Control of Cyclooxygenase-2 Expression through PPARγ*", The Journal of Biological Chemistry, vol. 275, No. 36, pp. 28028-28032, (2000).
Portanova, P. Joseph et al., "Selective Neutralization of Prostaglandin $E_2$ Blocks Inflammation, Hyperalgesia, and Interleukin 6 Production In Vivo", J. Exp. Med., vol. 184, No. 3, pp. 883-889, (Sep. 1996).
Ueno, Akinori et al., "Major roles of prostanoid receptors IP and $EP_3$ in endotoxin-induced enhancement of pain perception", Biochemical Pharmacology, vol. 62, No. 2, pp. 157-160, (2001).
Ushikubi, Fumitaka et al., "Impaired febrile response in mice lacking the prostaglandin E receptor subtype $EP_3$", Nature, vol. 395, pp. 281-284, (1998).
Fitzgerald, A. Garret et al., "The Coxibs, Selective Inhibitors of Cyclooxygenase-2", N Engl J Med., vol. 345, No. 6, pp. 433-442, (Aug. 9, 2001).
Malhotra, Samir et al., "COX-2 Inhibitors: A CLASS Act or Just VigorOUSLY Promoted", Medscape General Medicine, vol. 6, No. 1, 9 pages, (2004).
Mukherjee, Debabrata et al., "Commentary Cyclooxygenase-2: where are we in 2003? Cardiovascular risk and COX-2 inhibitors", Arthritis Research and Therapy, vol. 5, No. 1, pp. 8-11, (Oct. 28, 2002).
Stella, J. Valentino et al., "Prodrug strategies to overcome poor water solubility", Advanced Drug Delivery Reviews, vol. 59, pp. 677-694, (2007).
Block, H. Michael et al., "Discovery and Optimization of a Series of Carbazole Ureas as NPY5 Antagonists for the Treatment of Obesity", J. Med. Chem., vol. 45, pp. 3509-3523, (2002).
Thoren, Staffan et al., "Coordinate up- and down-regulation of glutathione-dependent prostaglandin E synthase and cyclooxygenase-2 in A549 cells Inhibition by NS-398 and leukotriene $C_4$", Eur. J. Biochem., vol. 267, pp. 6428-6434, (2000).
Stock, L. Jeffrey et al., "The prostaglandin $E_2$ EP1 receptor mediates pain perception and regulates blood pressure", The Journal of Clinical Investigation, vol. 107, No. 3, pp. 325-331, (Feb. 2001).
International Search Report issued Jul. 27, 2009 in PCT/EP09/55652 filed May 11, 2009.
Black et al. (Bioorg. Med. Chem. Lett. 13 (2003) 1195-1198).
Analytical Profiles of Drug Substances and Excipients, vol. 24, H. G. Brittain, Ed., Academic Press, London, p. 200 (1996).
S.K. Puri et al., Journal of Antimicrobial Chemotherapy, vol. 20, Suppl. B, pp. 89-100 (1987).
Bundgaard (Chapter 5 in "A Textbook of Drug Design and Development," (1991), Harwood Academic Publishers, 643 pages).

*Primary Examiner* — Robert Havlin
(74) *Attorney, Agent, or Firm* — Oblon, McClelland, Maier & Neustadt, L.L.P.

(57) ABSTRACT

The present invention relates to novel benzoyl derivatives of 3-aminocarbazole, to a pharmaceutical composition containing them, to a method for preparing them and to the use of such compounds for the production of a drug that is useful in the treatment or prevention of disturbances associated with the production of prostaglandin $E_2$ ($PGE_2$), for instance inflammatory processes, pain, fever, tumours, Alzheimer's disease and atherosclerosis.

3 Claims, No Drawings

3-AMINOCARBAZOLE COMPOUND, PHARMACEUTICAL COMPOSITION CONTAINING IT AND PREPARATION METHOD THEREFOR

CROSS REFERENCES TO RELATED APPLICATIONS

This application is a Continuation Application of U.S. patent application Ser. No. 12/991,815, filed on Nov.9, 2010, which was a 371 of International Patent Application No. PCT/EP09/055652, filed on May 11, 2009, and claims priority to European Patent Application No. 08425336.8, filed on May 14, 2008.

FIELD OF THE INVENTION

The present invention relates to novel 3-aminocarbazole compounds, to a pharmaceutical composition containing them, to a method for preparing them, and to the use of such compounds for the production of a drug that is useful in the treatment of disturbances associated with the production of prostaglandin $E_2$ ($PGE_2$), for instance inflammatory processes, pain, fever, tumours, Alzheimer's disease and atherosclerosis.

More particularly, the present invention relates to novel benzoyl derivatives of 3-aminocarbazole that are useful for treating or preventing disturbances associated with the production of prostaglandin $E_2$ ($PGE_2$), for instance inflammatory processes, pain, fever, tumours, Alzheimer's disease and atherosclerosis.

PRIOR ART

The value of the prostaglandin $E_2$ ($PGE_2$) arises from the role that they play as bioregulators, together with other prostanoids produced metabolically from arachidonic acid, and as inflammation mediators.

Prostanoids are a class of compounds including prostaglandins, thromboxanes and prostacyclins. Prostanoids are lipid mediators that act as local hormones on the cells adjacent to the site of their release. Prostanoids are mainly produced from arachidonic acid by cyclooxygenase-activated enzymatic oxidation. Cyclooxygenases (prostaglandin G/H synthases) catalyse the sequential formation of $PGG_2$ and $PGH_2$ from arachidonic acid. $PGH_2$ is then converted by means of specific enzymes into various prostanoids. The prostaglandin $D_2$ ($PGD_2$), prostaglandin $E_2$ ($PGE_2$), prostaglandin $F_{2\alpha}$ ($PGF_{2\alpha}$), prostaglandin $I_2$ ($PGI_2$) and thromboxane $A_2$ ($TXA_2$) are formed in this way.

With the exception of seminal fluid, prostanoids are not accumulated. Following various stimuli (inflammatory, immunological, hormonal, ultraviolet light, tumoral agents and also mechanical agitation), they are synthesized and released into the extracellular space, from where they pass into the plasma, the urine and other biological fluids.

Prostanoids play an important role in the defense mechanisms of the functioning of organs and in the integrity of the body. This is demonstrated by the cytoprotective function in the gastrointestinal tract, by the regulation of the renal function and of capillary circulation, by the regulation of platelet aggregation and blood clotting, the involvement in the differentiation of immune cells and in wound repair, bone metabolism and ovulation.

In particular, the vasoprotective action of the $PGI_2$, which are essential for maintaining vascular tonus and for preventing thromboembolism and atherosclerosis at the endothelial level, and the anti-inflammatory and antiproliferative action of the $PGD_2$, the metabolite of which, 15d-$PGJ_2$, is capable of exerting anti-inflammatory effects by means of activation of the PPARγ (peroxisome proliferator-activated receptor-gamma) nuclear receptors (Inoue et al., 2000, "Feedback control of cyclooxygenase-2 expression through PPAR-gamma" J. Biol. Chem. 2000, 275(36): 28028-28032), should be underlined.

Prostanoids are thus bioregulators, but also important mediators of inflammation and of other pathologies.

In particular, the $PGE_2$ are abundant at the sites of inflammation and are responsible for various pathological aspects of acute and chronic inflammation, for instance oedema, the formation of erythemas, inflammatory pain, articular inflammation and fever. In point of fact, the $PGE_2$ represent potent pro-inflammatory and algogenic agents. Anti-$PGE_2$ antibodies have anti-inflammatory activity and animals lacking $PGE_2$ receptors show a reduced response to inflammatory stimuli (Portanova et al., "Selective neutralization of prostaglandin E2 blocks inflammation, hyperalgesia, and interleukin 6 production in vivo", J. Exp. Med. 1996, 184(3): 883; Ueno et al., "Major roles of prostanoid receptors IP and EP(3) in endotoxin-induced enhancement of pain perception" Biochem. Pharmacol. 2001, 62(2): 157-160) and no febrile response to pyrogenic stimuli (Ushikubi et al., "Impaired febrile response in mice lacking the prostaglandin E receptor subtype EP3" Nature 1998, 395:281-284).

The non-steroidal anti-inflammatory drugs (NSAIDs) and selective COX-2 drugs currently in use reduce the inflammation-related symptoms by means of the non-selective inhibition of the production of eicosanoids ($PGE_2$, $PGD_2$, $PGF_{2\alpha}$, $PGI_2$ and $TXA_2$) on account of their inhibitory action on the cyclooxygenases 1 and 2 (Fitzgerald and Patrono, 2001).

In particular, the selective COX-2 drugs currently marketed have reduced gastrointestinal toxicity when compared with conventional non-steroidal anti-inflammatory drugs (NSAIDs). However, the said selective COX-2 drugs reduce the production of vascular prostacyclin ($PGI_2$, which is produced predominantly from COX-2), altering the normal equilibrium between the prothrombotic and antithrombotic eicosanoids in favour of the prothrombotic ($TXA_2$, which is produced predominantly from COX-1), and give rise to an increased risk of thrombotic-cardiovascular events (S. Malhotra, MD, DM; N. Shafiq, MD; P. Pandhi, MD Medscape General Medicine 6(1), 2004; D. Mukherjee and E. J. Topol Cardiovascular risk and COX-2 inhibitors, Arthritis Res. Ther. 2003, 5:8-11-2002).

Various 3-aminocarbazole compounds have been studied for their ability to selectively bind to the human Y5 receptor and to modulate its activity. This ability makes them useful in the treatment of appetite and metabolic disorders, for instance obesity, bulimia nervosa, anorexia nervosa, sleep disturbances, morphine dependency and epileptic attacks (WO 01/07409 A1, WO 02/051806, WO 02/096902 and U.S. Pat. No. 6,399,631).

Patent application WO 2006/122 680 describes the use of a number of 3-aminocarbazole compounds for treating disturbances related to the production of prostaglandin $E_2$ ($PGE_2$). In addition, patent application WO 2007/014 687 describes a number of novel 3-aminocarbazole compounds and their use for treating disturbances related to the production of prostaglandin $E_2$ ($PGE_2$).

SUMMARY OF THE INVENTION

It has now been found, surprisingly, that certain novel 3-aminocarbazole compounds, besides being capable of selectively inhibiting the production of prostaglandin $E_2$ ($PGE_2$), have shown, surprisingly, improved bioavailability and pharmacokinetic properties.

These compounds are capable of reducing the production of $PGE_2$ and are thus active in all the pathological conditions in which $PGE_2$ acts as a mediator, for instance inflammatory processes, pain, fever, tumours, Alzheimer's disease and atherosclerosis.

In addition, these compounds have shown, surprisingly, high metabolic stability, high absorption in vitro and high bioavailability.

Typical examples of such inflammatory processes are oedema, erythema, articular inflammation, rheumatoid arthritis and arthrosis.

Typical examples of such tumours are colorectal and pulmonary carcinoma and adenocarcinoma.

The compounds of the present invention selectively inhibit the synthesis of $PGE_2$. This selectivity has the advantage of inhibiting a potent mediator of inflammation, pain and fever, while leaving unaltered the production of the other prostanoids produced simultaneously in the arachidonic acid cascade, such as $PGF_{2\alpha}$, $TXA_2$, $PGI_2$ and $PGD_2$. All the defense mechanisms of the functioning of organs and of the integrity of the body that are typical of the activity of the other prostanoids thus remain unchanged.

Similarly to conventional non-steroidal anti-inflammatory drugs, the compounds of the present invention have anti-inflammatory, antipyretic and analgesic properties, and are thus active in pathologies such as inflammation, pain, fever, rheumatoid arthritis and arthrosis. In addition, since the involvement of $PGE_2$ in tumours, Alzheimer's disease and atherosclerosis is known in the literature, the compounds of the present invention also have applications in the prevention and treatment of these pathologies.

Advantageously, these compounds however show few side effects when compared with NSAIDs and selective COX-2 drugs, which, by inhibiting cyclooxygenases, do not discriminate between the prostanoids.

In particular, these compounds are useful in both the treatment and the prevention of inflammatory processes.

In particular, the compounds of the present invention show reduced gastrointestinal, renal and vascular toxicity.

DETAILED DESCRIPTION OF THE INVENTION

In a first aspect, the present invention relates to a 3-aminocarbazole compound having the general formula (I) below:

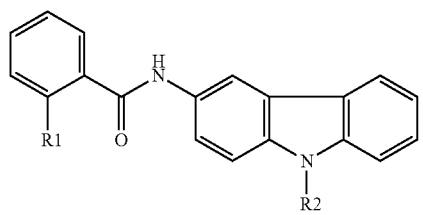

(I)

in which
R1 is a halogen atom, a methyl group or a trihalomethyl group, a nitro group, a cyano group or a triflate group, and
R2 is a linear or branched hydroxyalkyl group comprising from 1 to 8 carbon atoms or a linear or branched carbonylalkyl group comprising from 1 to 8 carbon atoms, or a pharmaceutically acceptable salt thereof, a polymorphic crystal form thereof, a stereoisomer thereof or an enantiomer thereof.

In particular, the present invention relates to 3-aminocarbazole compounds of general formula (I) in which R1 is a fluorine or chlorine atom, or a trifluoromethyl or trichloromethyl group, and R2 is a linear or branched hydroxyalkyl group comprising from 1 to 6 carbon atoms or a linear or branched carbonylalkyl group comprising from 1 to 4 carbon atoms.

For the purposes of the present invention, the term "hydroxyalkyl" means an alkyl group comprising from 1 to 3 hydroxyl groups (—OH) bonded to one or more carbon atoms, and the term "carbonylalkyl" means an alkyl group comprising from 1 to 3 oxy groups (=O) bonded to one or more carbon atoms.

According to the preferred aspect, the present invention relates to 3-aminocarbazole compounds of general formula (I) in which R1 and R2 have the meaning given in Table 1 below.

TABLE 1

| Compound | R1 | R2 |
|---|---|---|
| 1 | $CF_3$ | $CH_2CH_2OH$ |
| 2 | $CF_3$ | $CH_2C(CH_3)_2OH$ |
| 3 | $CF_3$ | $CH_2CH_2C(CH_3)_2OH$ |
| 4 | $CF_3$ | $CH_2COCH_3$ |
| 5 | Cl | $CH_2CH_2OH$ |
| 6 | Cl | $CH_2CH_2C(CH_3)_2OH$ |

Formula (I) described previously comprises compounds in which the phenyl group bears, besides R1, one or more substituents such as, for example, a halogen atom, an alkyl group comprising from 1 to 3 carbon atoms, a trifluoromethyl group, a nitro group, a triflate group ($CF_3SO_3$—), an alkyl-carboxyl group comprising from 1 to 3 carbon atoms (—$(CH_2)_n$COOH), an amide group (—$CONH_2$), a methylsulfoxy group (—$SO_2CH_3$), an N-methylsulfonamide group —$SO_2NHCH_3$ or a methanesulfonamide group $NHSO_2CH_3$.

As is known to those skilled in the art, the pharmaceutically acceptable salts of the compounds of general formula (I) may be base-addition salts. Examples of suitable pharmaceutically acceptable bases are alkali metals and alkaline-earth metals such as $Na^+$, $K^+$, $Mg^{++}$, $Ca^{++}$ and organic bases such as tromethamine, choline and lysine.

The compounds of general formula (I) according to the present invention may have more than one crystal structure or form, or may be in amorphous form. The compounds that have this characteristic are commonly referred to as polymorphs. Different polymorphs of this compound may exhibit different chemical, physical and spectroscopic properties.

In addition, in the case of certain substituents, the compounds of general formula (I) according to the present invention may have one or more asymmetric carbon atoms and may thus be in the form of stereoisomers and enantiomers.

Thus, the compounds of the present invention also include the pharmaceutically acceptable salts, the polymorphic crystal forms, the stereoisomers and the enantiomers of a compound represented by formula (I) described in the claims.

In a second aspect, the present invention relates to a pharmaceutical composition characterized in that it comprises a therapeutically effective dose of a 3-aminocarbazole compound having the abovementioned general formula (I) or a pharmaceutically acceptable salt thereof together with at least one pharmaceutically acceptable inert vehicle.

Preferably, the pharmaceutical compositions of the present invention are prepared in suitable dosage forms.

Examples of suitable dosage forms are tablets, capsules, coated tablets, granules, and solutions and syrups for oral administration; creams, ointments and antiseptic plasters for topical administration; suppositories for rectal administration and sterile solutions for administration by injection, or aerosol or ophthalmic administration.

Advantageously, these dosage forms are formulated so as to ensure a controlled release over time of a compound of the abovementioned general formula (I) or of a pharmaceutically acceptable salt thereof. Specifically, depending on the type of therapy, the required release time may be very short, normal or long.

The dosage forms may also contain other conventional ingredients, for instance: preserving agents, stabilizers, surfactants, buffers, salts for regulating the osmotic pressure, emulsifiers, sweeteners, dyes, flavourings and the like.

In addition, when required for particular therapies, the pharmaceutical composition of the present invention may also contain other pharmacologically active ingredients whose simultaneous administration is useful.

Advantageously, the pharmaceutical composition of the present invention may contain a prodrug of a compound of formula (I). The prodrug of a compound of formula (I) is a substance in substantially inactive form which, when administered to a living being, is metabolized into a compound of formula (I). As is known to those skilled in the art, the prodrug of the compounds of general formula (I) may be ester derivatives obtained by reacting the hydroxy group of R2 with an acid, such as a monocarboxylic acid, a bicarboxylic acid, a fatty acid, an aminoacid, an (alkyl)phosphoric acid, or an (alkyl)tiophosphoric acid. Examples of suitable prodrugs are acetyl ester, propionyl ester, succinyl ester, stearate ester, palmitate ester, glycine ester, leucine ester, lysine ester, phosphate ester, methylphosphate ester, methyltiophosphate ester, and phosphonate ester. Useful examples of suitable prodrugs are described, for example, in Stella V. J. et al, "Prodrug strategies to overcome poor water solubility", Advance Drug Delivery Reviews 59 (2007) 677-694. The composition of the present invention may also include the pharmaceutically acceptable salts, polymorphic crystal forms, stereoisomers and enantiomers of the prodrug of a compound represented by formula (I) described in the claims.

The amount of the compound of the present invention in the pharmaceutical composition may vary within a wide range as a function of known factors, for instance the type of disease to be treated, the severity of the disease, the body weight of the patient, the dosage form, the selected route of administration, the number of daily administrations and the efficacy of the selected compound. However, the optimum amount may be readily and routinely determined by a person skilled in the art.

Typically, the amount of compound of the present invention in the pharmaceutical composition will be such that it ensures a level of administration of between 0.0001 and 100 mg/kg/day and even more preferably between 0.01 and 10 mg/kg/day.

The dosage forms of the pharmaceutical composition of the present invention may be prepared according to techniques that are well known to pharmaceutical chemists, including mixing, granulation, tabletting, dissolution, sterilization and the like.

In a third aspect, the present invention relates to a method for treating or preventing inflammatory processes, pain, fever, tumours, Alzheimer's disease and atherosclerosis in mammals, comprising the administration of a therapeutically effective amount of a 3-aminocarbazole compound having the abovementioned general formula (I), a pharmaceutically acceptable salt thereof, a polymorphic crystal form thereof, a stereoisomer thereof or an enantiomer thereof, to a person in need thereof.

Preferably, the inflammatory process is chosen from the group comprising oedema, erythema, articular inflammation, rheumatoid arthritis and arthrosis, and the tumour is chosen from the group comprising colorectal or pulmonary carcinoma and adenocarcinoma.

The 3-aminocarbazoles having the abovementioned general formula (I) may be prepared according to known methods, for instance by reacting an acid, or a reactive derivative thereof, with the selected amine (patent application WO 02/096902 A1, WO 02/051806, J. Med. Chem. 2002 vol. 45, pp. 3509-3523). Typical examples of reactive derivatives are acyl halides, anhydrides or esters.

In a fourth aspect, the present invention thus relates to a method for preparing a 3-aminocarbazole having the abovementioned general formula (I), characterized in that it comprises the following stages:

a) reaction of an amine of formula (II)

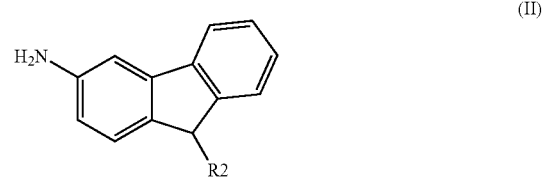

in which R2 has the meaning given previously,
with a compound of formula (III)

in which R1 has the meaning given previously, and
Z is chosen from the group comprising Cl, Br, OH, OR and OC(O)R, in which R is a linear or branched alkyl having from 1 to 6 carbon atoms, to give a 3-aminocarbazole compound of formula (I)

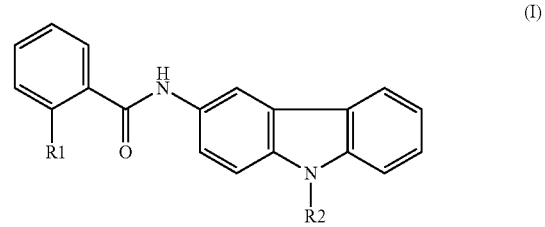

in which R1 and R2 have the meanings given previously, and
b) optional formation of a pharmaceutically acceptable salt, a polymorphic crystal form, a stereoisomer or an enantiomer of the compound of formula (I) thus obtained.

Typically, step (a) is performed in the presence of a suitable diluent at a temperature within the range between 0 and 140° C., for a time within the range between 0.5 and 24 hours.

Preferably, the reaction temperature is within the range between 15 and 40° C. Advantageously, the reaction time ranges from 2 to 18 hours.

Preferably, the diluent is aprotic, polar or apolar. Even more preferably, it is a polar aprotic diluent. Examples of suitable polar aprotic diluents are dimethylformamide and dichloromethane.

In the embodiment in which Z is Cl or Br, the reaction is advantageously performed in the presence of a suitable organic or inorganic acid acceptor. Examples of suitable organic acceptors are diisopropylethylenediamine, triethyleneamine, pyridine and dimethylaminopyridine. Examples of suitable inorganic acceptors are alkali metal carbonates or bicarbonates.

In the embodiment in which Z is OH, the reaction is preferably performed in the presence of a suitable coupling agent, for instance dicyclohexylcarbodiimide (also supported on polystyrene resin) or carbonyldiimidazole.

The examples that follow are given to illustrate the invention in greater detail without, however, limiting it.

EXAMPLE 1

Preparation of Compound 1

R1=$CF_3$, R2=$CH_2CH_2OH$ a) 2-(3-nitro-9H-carbazol-9-yl)ethanol

To a solution of 2-(9H-carbazol-9-yl)ethanol (25 g; 0.12 mol) in glacial acetic acid (374 ml) was added dropwise over 30 minutes a solution containing nitric acid (6.8 ml; 0.17 mol) in glacial acetic acid (20 ml), with vigorous stirring. Five minutes after completion of the addition, a green precipitate separated out. The reaction mixture was poured slowly into $H_2O$ and ice (1 L), stirred for 1 hour, filtered and finally washed with $H_2O$. The solid separated out was taken up first in $H_2O$ (500 ml) and then with 10% sodium carbonate solution to obtain a pH of 7, and finally filtered off. The solid obtained was crystallized from a solution of acetone/absolute ethanol (1:1) to give 20 g of 2-(3-nitro-9H-carbazol-9-yl) ethanol $^1$H NMR (300 MHz, DMSO-$d_6$) δ 9.16 (d, J=2.34 Hz, 1H), 8.40 (d, J=7.75 Hz, 1H), 8.33 (dd, J=2.34, 9.21 Hz, 1H), 7.79 (d, J=9.06 Hz, 1H), 7.73 (d, J=8.33 Hz, 1H), 7.57 (ddd, J=1.24, 7.13, 8.29 Hz, 1H), 7.33 (ddd, J=0.95, 7.13, 7.86 Hz, 1H), 4.89 (t, J=5.90 Hz, 1H), 4.54 (t, J=5.41 Hz, 2H), 3.82 (q, J=5.41 Hz, 2H).

b) 2-(3-amino-9H-carbazol-9-yl)ethanol hydrochloride

The product obtained as described in the preceding step a) (10 g; 0.04 mol) was dissolved in tetrahydrofuran (550 ml). Stannous chloride dihydrate (87 g; 0.4 mol) was then added. The mixture thus obtained was refluxed for 16 hours.

The reaction mixture was allowed to cool to room temperature and the solvent was then removed under reduced pressure. The residue was taken up in $H_2O$ and dichloromethane, and stirred vigorously. The pH was brought to 7.5 by adding saturated sodium bicarbonate solution, the mixture was filtered through Celite and the filtrate transferred into a separating funnel. The organic phase was separated out and dried over $Na_2SO_4$. The solvent was removed by evaporation under reduced pressure and the residue thus obtained (9 g) was dissolved in ethanol and converted into the corresponding hydrochloride by adding ethanolic 5 M hydrogen chloride solution. The precipitated solid was filtered off to give 2-(3-amino-9H-carbazol-9-yl)ethanol hydrochloride (9 g).

$^1$H NMR (300 MHz, DMSO-$d_6$) δ 10.41 (broad s, 3H), 8.17 (d, J=7.76 Hz, 1H), 8.12 (d, J=1.98 Hz, 1H), 7.73 (d, J=8.75 Hz, 1H), 7.66 (d, J=8.26 Hz, 1H), 7.38-7.56 (m, 2H), 7.23 (t, J=7.27 Hz, 1H), 4.70 (broad s, 1H), 4.47 (t, J=5.53 Hz, 2H), 3.78 (t, J=5.45 Hz, 2H).

c) N-[9-(2-hydroxyethyl)-9H-carbazol-3-yl]-2-(trifluoromethyl)benzamide

The product obtained as described in the preceding step b) (26 g; 0.1 mol) was suspended in dichloromethane (300 ml). Triethylamine (28 ml; 0.2 mol) and 2-trifluoromethylbenzoyl chloride (15.6 ml; 0.11 mol) were then added to the solution. The mixture thus obtained was stirred at room temperature for 16 hours.

The solvent was evaporated off under reduced pressure, the residue was taken up in 2N NaOH solution (200 ml), and the resulting solution was refluxed for 2 hours. The suspension thus obtained was poured into water and the product was filtered off, dried and crystallized from an isopropyl ether/isopropanol mixture (1:1).

N[9-(2-Hydroxyethyl)-9H-carbazol-3-yl]-2-(trifluoromethyl)benzamide (24 g) was thus obtained.

m.p.: 176-177° C.

Elemental analysis for $C_{22}H_{17}F_3N_2O_2$

|  | C | H | N |
|---|---|---|---|
| Found % | 66.14 | 4.06 | 6.85 |
| Calculated % | 66.33 | 4.30 | 7.03 |

$^1$H NMR (300 MHz, DMSO-$d_6$) δ 10.52 (s, 1H), 8.50 (d, J=1.75 Hz, 1H), 8.08 (d, J=7.31 Hz, 1H), 7.54-7.93 (m, 7H), 7.44 (t, J=7.02 Hz, 1H), 7.18 (t, J=7.45 Hz, 1H), 4.85 (t, J=5.45 Hz, 1H), 4.43 (t, J=5.70 Hz, 2H), 3.79 (q, J=5.75 Hz, 2H).

EXAMPLE 2

Preparation of Compound 2

R1=$CF_3$, R2=$CH_2C(CH_3)_2OH$ a) 1-(9H-carbazol-9-yl)-2-methylpropan-2-ol

To a solution containing carbazole (20 g; 0.12 mol) in DMSO (300 ml) was added 50% sodium hydroxide solution (300 ml), benzyltrimethylammonium chloride (5.5 g; 0.024 mol) and, dropwise, 2-chloro-2-methylpropan-2-ol (39.1 g; 0.36 mol). The mixture thus obtained was stirred at room temperature for 16 hours.

The mixture was poured into $H_2O$ and ice (3 L), stirred for 1 hour and filtered, and the solid obtained was crystallized from a hexane/ethyl acetate mixture (9:1) to give 1-(9H-carbazol-9-yl)-2-methylpropan-2-ol (15 g).

$^1$H NMR (300 MHz, DMSO-$d_6$) δ 8.07-8.15 (m, 2H), 7.68 (d, J=8.33 Hz, 2H), 7.40 (ddd, J=1.24, 7.13, 8.29 Hz, 2H), 7.13-7.20 (m, 2H), 4.64 (s, 1H), 4.26 (s, 2H), 1.21 (s, 6H).

b) 1-(3-nitro-9H-carbazol-9-yl)-2-methylpropan-2-ol

To a solution of the product obtained as described in the preceding step a) (21 g; 0.088 mol) in glacial acetic acid (400 ml) was added dropwise over 30 minutes a solution containing nitric acid (5 ml; 0.123 mol) in glacial acetic acid (15 ml; 0.263 mol) with vigorous stirring. 5 minutes after completion of the addition, a green precipitate separated out. The reaction mixture was poured slowly into $H_2O$ and ice (1 L), stirred for 1 hour, filtered and finally washed with $H_2O$. The solid separated out was taken up first in $H_2O$ (500 ml) and then in 10% sodium carbonate solution until a pH of 7 was obtained, and finally filtered off.

The solid obtained was crystallized from an ethyl acetate/ethanol mixture (8:2) to give 1-(3-nitro-9H-carbazol-9-yl)-2-methylpropan-2-ol (19 g).

¹H NMR (300 MHz, DMSO-$d_6$) δ 9.15 (d, J=2.05 Hz, 1H), 8.38 (d, J=7.31 Hz, 1H), 8.30 (dd, J=2.48, 9.21 Hz, 1H), 7.87 (d, J=9.06 Hz, 1H), 7.81 (d, J=8.48 Hz, 1H), 7.54 (ddd, J=1.17, 7.16, 8.33 Hz, 1H), 7.31 (td, J=0.88, 7.60 Hz, 1H), 4.73 (s, 1H), 4.37 (s, 2H), 1.21 (s, 6H).

c) 1-(3-amino-9H-carbazol-9-yl)-2-methylpropan-2-ol hydrochloride

The product obtained as described in the preceding step b) (7.9 g; 0.028 mol) was dissolved in tetrahydrofuran (350 ml). Stannous chloride dihydrate (62.8 g; 0.28 mol) was then added. The mixture thus obtained was refluxed for 16 hours.

The reaction mixture was allowed to cool to room temperature and the solvent was then removed under reduced pressure. The residue was taken up in $H_2O$ and dichloromethane, and subjected to vigorous stirring. The pH was brought to 7.5 by adding saturated sodium bicarbonate solution, the mixture was filtered through Celite and the filtrate transferred into a separating funnel. The organic phase was separated out and dried over $Na_2SO_4$. The solvent was removed by evaporation under reduced pressure and the residue thus obtained (9 g) was dissolved in ethanol and converted into the corresponding hydrochloride by adding ethanolic 5 M hydrogen chloride solution. The solid obtained was crystallized from an isopropanol/water mixture (8:2) to give 1-(3-amino-9H-carbazol-9-yl)-2-methylpropan-2-ol hydrochloride (6 g).

¹H NMR (300 MHz, DMSO-$d_6$) δ 10.32 (broad s, 3H), 8.16 (d, J=7.60 Hz, 1H), 8.10 (d, J=2.31 Hz, 1H), 7.81 (d, J=8.92 Hz, 1H), 7.74 (d, J=8.26 Hz, 1H), 7.47 (ddd, J=0.99, 7.10, 8.42 Hz, 1H), 7.42 (dd, J=2.15, 8.75 Hz, 1H), 7.22 (t, J=7.43 Hz, 1H), 4.70 (broad s, 1H), 4.30 (s, 2H), 1.20 (s, 6H).

d) N-[9-(2-hydroxy-2-methylpropyl)-9H-carbazol-3-yl]-2-(trifluoro-methyl)benzamide The product obtained as described in the preceding step c) (3.3 g; 0.011 mol) was suspended in dichloromethane (30 ml). Triethylamine (3 ml; 0.022 mol) and 2-trifluoromethylbenzoyl chloride (1.7 ml; 0.012 mol) were then added to the solution. The mixture thus obtained was stirred at room temperature for 16 hours.

The solvent was evaporated off under reduced pressure, the residue was taken up in 2N NaOH solution (20 ml) and the resulting solution was refluxed for 2 hours. The suspension thus obtained was poured into water and the product was filtered off, dried and crystallized from an isopropyl ether/isopropanol mixture (1:1).

N-[9-Hydroxy-2-methylpropyl)-9H-carbazol-3-yl]-2-(trifluoromethyl)-benzamide (2.7 g) was thus obtained.

m.p.: 179-181° C.

Elemental analysis for $C_{24}H_{21}F_3N_2O_2$

|  | C | H | N |
|---|---|---|---|
| Found % | 67.51 | 4.82 | 6.52 |
| Calculated % | 67.60 | 4.96 | 6.57 |

¹H NMR (300 MHz, DMSO-$d_6$) δ 10.50 (s, 1H), 8.49 (s, 1H), 8.06 (d, J=7.93 Hz, 1H), 7.56-7.92 (m, 7H), 7.42 (t, J=7.76 Hz, 1H), 7.17 (t, J=7.43 Hz, 1H), 4.65 (s, 1H), 4.26 (s, 2H), 1.21 (s, 6H).

EXAMPLE 3

Preparation of Compound 3

R1=$CF_3$, R2=$CH_2CH_2C(CH_3)_2OH$ a) Ethyl 3-(9H-carbazol-9-yl)propanoate

To a solution containing carbazole (20 g; 0.12 mol) in DMF (130 ml) was added portionwise sodium hydride (50% suspension) (6.7 g; 0.14 mol); the suspension thus obtained was stirred at room temperature for 30 minutes and then heated to 60° C. A solution containing ethyl 3-bromopropanoate (17.9 ml; 0.14 mol) in DMF (20 ml) was added dropwise and the mixture was stirred for 16 hours.

The mixture was poured into $H_2O$ (0.5 L) and filtered. The solid obtained was purified by flash chromatography on silica, using as eluent a hexane/ethyl acetate mixture (8:2) to give 16 g of ethyl 3-(9H-carbazol-9-yl)propanoate, which product was used in the subsequent reaction without further purification.

b) 4-(9H-carbazol-9-yl)-2-methylbutan-2-ol

To a solution of the product obtained in the preceding step a) (15.2 g; 0.057 mol) in tetrahydrofuran (200 ml) was added a 3M solution of methylmagnesium iodide in diethyl ether (57 ml; 0.171 mol). The mixture thus obtained was stirred at room temperature for 16 hours. 1M $NH_4Cl$ solution (500 ml) was then added to the mixture. The resulting mixture was transferred into a separating funnel and extracted with ethyl acetate. The organic phase was dried over $Na_2SO_4$ and the solvent evaporated off under reduced pressure. The residue obtained was crystallized from a hexane/ethyl acetate mixture (8:2) to give 4-(9H-carbazol-9-yl)-2-methylbutan-2-ol (9 g), which product was used in the subsequent reaction without further purification.

c) 2-methyl-4-(3-nitro-9H-carbazol-9-yl)butan-2-ol

The product obtained in the preceding step b) (7.2 g; 0.028 mol) was reacted by working in a manner similar to that described in Example 1a). The product obtained was crystallized from ethyl acetate to give 2-methyl-4-(3-nitro-9H-carbazol-9-yl)butan-2-ol (6 g).

¹H NMR (300 MHz, DMSO-$d_6$) δ 9.17 (d, J=2.34 Hz, 1H), 8.41 (d, J=7.60 Hz, 1H), 8.36 (dd, J=2.34, 9.35 Hz, 1H), 7.73 (d, J=9.35 Hz, 1H), 7.66-7.71 (m, 1H), 7.56-7.64 (m, 1H), 7.31-7.38 (m, 1H), 4.62 (s, 1H), 4.48-4.58 (m, 2H), 1.79-1.89 (m, 2H), 1.24 (s, 6H).

d) 4-(3-amino-9H-carbazol-9-yl)-2-methylbutan-2-ol hydrochloride

To a suspension of the product obtained in the preceding step c) (5.9 g; 0.020 mol) in 95° ethanol (80 ml) was added 10% Pd/C (0.5 g; 0.0005 mol) and the mixture was subjected to hydrogenation in a Parr hydrogenator (30 psi) for 4 hours. The reaction mixture was filtered, the solution was evaporated under reduced pressure and the product obtained was dissolved in ethyl acetate and converted into the corresponding hydrochloride by adding ethanolic 5M hydrogen chloride solution. The solid thus obtained was crystallized from an isopropyl ether/isopropanol mixture (1:1) to give 4-(3-amino-9H-carbazol-9-yl)-2-methylbutan-2-ol hydrochloride (5.5 g).

¹H NMR (300 MHz, DMSO-$d_6$) δ 10.34 (broad s, 3H), 8.19 (d, J=7.60 Hz, 1H), 8.13 (d, J=1.98 Hz, 1H), 7.68 (d, J=8.92 Hz, 1H), 7.62 (d, J=8.20 Hz, 1H), 7.44-7.58 (m, 2H), 7.25 (t, J=6.94 Hz, 1H), 4.08-4.83 (m, 3H), 1.73-1.88 (m, 2H), 1.23 (s, 6H).

e) N-[9-(3-hydroxy-3-methylbutyl)-9H-carbazol-3-yl]-2-trifluoromethyl-benzamide

The product obtained as described in the preceding step d) (3.9 g; 0.013 mol) was reacted by working in a manner similar to that described in Example 1c).

The solid obtained was crystallized from ethanol to give N-[9-(3-hydroxy-3-methylbutyl)-9H-carbazol-3-yl]-2-(trifluoromethyl)benzamide (2.3 g).

m.p.: 188-189° C.

Elemental analysis for $C_{25}H_{23}F_3N_2O_2$

|  | C | H | N |
|---|---|---|---|
| Found % | 67.75 | 5.31 | 6.23 |
| Calculated % | 68.17 | 5.26 | 6.36 |

$^1$H NMR (300 MHz, DMSO-d$_6$) δ 10.53 (s, 1H), 8.52 (d, J=1.98 Hz, 1H), 8.10 (d, J=7.60 Hz, 1H), 7.68-7.90 (m, 4H), 7.66 (dd, J=2.00, 8.70 Hz, 1H), 7.52-7.59 (m, 2H), 7.47 (t, J=7.10 Hz, 1H), 7.19 (t, J=7.43 Hz, 1H), 4.55 (s, 1H), 4.38-4.51 (m, 2H), 1.71-1.91 (m, 2H), 1.23 (s, 6H).

EXAMPLE 4

Preparation of Compound 4

R1=CF$_3$, R2=CH$_2$COCH$_3$ a) Ethyl 9H-carbazol-9-ylacetate

To a solution containing carbazole (20 g; 0.12 mol) in DMF (130 ml) was added portionwise sodium hydride (50% suspension) (6.9 g; 0.14 mol); the suspension thus obtained was stirred at room temperature for 30 minutes and then heated to 60° C. A solution containing ethyl 2-bromoacetate (24 g; 0.14 mol) in DMF (20 ml) was added dropwise, and the resulting mixture was stirred for 16 hours. The mixture was poured into H$_2$O (0.5 L) and filtered, and the solid obtained was crystallized from hexane to give ethyl 9H-carbazol-9-ylacetate (20 g).

$^1$H NMR (300 MHz, DMSO-d$_6$) δ 8.15 (d, J=7.60 Hz, 2H), 7.54 (d, J=8.20 Hz, 2H), 7.43 (td, J=1.02, 7.67 Hz, 2H), 7.17-7.27 (m, 2H), 5.33 (s, 2H), 4.14 (q, J=7.02 Hz, 2H), 1.20 (t, J=7.16 Hz, 3H).

b) 1-(9H-carbazol-9-yl)acetone

To a solution of the product obtained in the preceding step a) (14.1 g; 0.056 mol) in tetrahydrofuran (130 ml) was added a 3M solution of methylmagnesium iodide in diethyl ether (28 ml; 0.084 mol). The mixture thus obtained was stirred at room temperature for 16 hours. 1M NH$_4$Cl solution (100 ml) was then added to the mixture. The resulting mixture was transferred into a separating funnel and extracted with ethyl acetate. The organic phase was dried over Na$_2$SO$_4$ and the solvent was evaporated off under reduced pressure. The residue obtained was purified by flash chromatography on silica, using as eluent a hexane/ethyl acetate mixture (95:5) to give 1-(9H-carbazol-9-yl)acetone (8 g), which product was used without further purification in the subsequent reaction.

$^1$H NMR (300 MHz, DMSO-d$_6$) δ 8.15 (d, J=7.89 Hz, 2H), 7.49 (d, J=8.20 Hz, 2H), 7.41 (ddd, J=1.10, 7.00, 8.20 Hz, 2H), 7.21 (ddd, J=1.10, 7.00, 7.89 Hz, 2H), 5.39 (s, 2H), 2.24 (s, 3H).

c) 1-(3-nitro-9H-carbazol-9-yl)acetone

The product obtained in the preceding step b) (5 g; 0.022 mol) was reacted by working in a manner similar to that described in Example 1a). The residue obtained was purified by flash chromatography on silica, using as eluent an 8:2 hexane/ethyl acetate mixture to give 1-(3-nitro-9H-carbazol-9-yl)acetone (4.5 g), which product was used without further purification for the subsequent reaction.

$^1$H NMR (300 MHz, DMSO-d$_6$) δ 9.20 (d, J=2.34 Hz, 1H), 8.42 (d, J=7.89 Hz, 1H), 8.33 (dd, J=2.34, 9.06 Hz, 1H), 7.70 (d, J=9.35 Hz, 1H), 7.60-7.67 (m, 1H), 7.54 (td, J=1.17, 7.75 Hz, 1H), 7.30-7.39 (m, 1H), 5.57 (s, 2H), 2.32 (s, 3H).

d) 1-(3-amino-9H-carbazol-9-yl)acetone hydrochloride

To a suspension of the product obtained in the preceding step c) (1.3 g; 0.005 mol) in 95° ethanol (80 ml) was added 10% Pd/C (0.5 g; 0.0005 mol) and the mixture was subjected to hydrogenation in a Parr hydrogenator (30 psi) for 4 hours. The reaction mixture was filtered and the solution was evaporated under reduced pressure. The product obtained was dissolved in ethyl acetate and converted into the corresponding hydrochloride by adding ethanolic 5M hydrogen chloride solution. The solid precipitated out was filtered off to give 1-(3-amino-9H-carbazol-9-yl)acetone hydrochloride (1.1 g).

$^1$H NMR (300 MHz, DMSO-d$_6$) δ 10.39 (broad s, 3H), 8.19 (d, J=7.60 Hz, 1H), 8.14 (d, J=1.98 Hz, 1H), 7.62 (d, J=8.59 Hz, 1H), 7.52-7.58 (m, 1H), 7.40-7.52 (m, 2H), 7.25 (ddd, J=0.99, 6.94, 7.93 Hz, 1H), 5.46 (s, 2H), 2.27 (s, 3H).

e) N-[9-(2-oxopropyl)-9H-carbazol-3-yl]-2-(trifluoromethyl)benzamide

The product obtained in the preceding step d) (1.1 g; 0.004 mol) was reacted by working in a manner similar to that described in Example 1c).

The solid obtained was crystallized from an isopropyl ether/isopropanol mixture (1:1) to give N-[9-(2-oxopropyl)-9H-carbazol-3-yl]-2-(trifluoromethyl)benzamide (1.2 g).

m.p.: 223-226° C.

Elemental analysis for C$_{23}$H$_{17}$F$_3$N$_2$O$_2$

|  | C | H | N |
| --- | --- | --- | --- |
| Found % | 67.02 | 3.91 | 6.78 |
| Calculated % | 67.31 | 4.18 | 6.83 |

$^1$H NMR (300 MHz, DMSO-d$_6$) δ 10.52 (s, 1H), 8.50 (d, J=1.75 Hz, 1H), 8.10 (d, J=7.60 Hz, 1H), 7.66-7.91 (m, 4H), 7.61 (dd, J=2.05, 8.77 Hz, 1H), 7.36-7.53 (m, 3H), 7.20 (t, J=6.87 Hz, 1H), 5.38 (s, 2H), 2.24 (s, 3H).

EXAMPLE 5

Preparation of Compound 5

R1=Cl, R2=CH$_2$CH$_2$OH a) 2-chloro-N-[9-(2-hydroxyethyl)-9H-carbazol-3-yl]benzamide The product obtained as described in Example 1b) (6.4 g; 0.028 mol) was suspended in dichloromethane (70 ml). Triethylamine (7.9 ml; 0.2 mol) and 2-chlorobenzoyl chloride (3.95 ml; 0.031 mol) were then added to the solution. The mixture thus obtained was stirred at room temperature for 16 hours.

The solvent was evaporated off under reduced pressure, the residue was taken up in 2N NaOH solution (80 ml), and the resulting solution was refluxed for 2 hours. The suspension thus obtained was poured into water, and the product filtered off, dried and crystallized from 95° ethanol.

2-Chloro-N-[9-(2-hydroxyethyl)-9H-carbazol-3-yl]benzamide (5.5 g) was thus obtained.

m.p.: 168-169° C.

Elemental analysis for C$_{21}$H$_{17}$ClN$_2$O$_2$

|  | C | H | N |
| --- | --- | --- | --- |
| Found % | 68.83 | 4.63 | 7.58 |
| Calculated % | 69.14 | 4.70 | 7.68 |

$^1$H NMR (300 MHz, DMSO-d$_6$) δ 10.47 (s, 1H), 8.55 (d, J=1.98 Hz, 1H), 8.08 (d, J=7.27 Hz, 1H), 7.39-7.71 (m, 8H), 7.18 (t, J=7.43 Hz, 1H), 4.86 (t, J=5.45 Hz, 1H), 4.43 (t, J=5.78 Hz, 2H), 3.78 (q, J=5.83 Hz, 2H).

EXAMPLE 6

Preparation of Compound 6

R1=Cl, R2=CH$_2$CH$_2$C(CH$_3$)$_2$OH a) 2-chloro-N-[9-(3-hydroxy-3-methylbutyl)-9H-carbazol-3-yl]benzamide The product obtained as described in Example 3d) (1.1 g; 0.0037 mol) was reacted with 2-chlorobenzoyl chloride (0.52 ml; 0.0041 mol), by working in a manner similar to that described in Example 1c).

The solid obtained was crystallized from ethyl acetate to give 2-chloro-N-[9-(3-hydroxy-3-methylbutyl)-9H-carbazol-3-yl]benzamide (0.63 g).

m.p.: 120-124° C.

Elemental analysis for C$_{24}$H$_{23}$ClN$_2$O$_2$

|  | C | H | N |
|---|---|---|---|
| Found % | 70.52 | 5.62 | 6.71 |
| Calculated % | 70.84 | 5.70 | 6.88 |

$^1$H NMR (300 MHz, DMSO-d$_6$) δ 10.48 (s, 1H), 8.57 (d, J=1.98 Hz, 1H), 8.09 (d, J=7.60 Hz, 1H), 7.41-7.73 (m, 8H), 7.19 (t, J=7.43 Hz, 1H), 4.55 (s, 1H), 4.37-4.51 (m, 2H), 1.73-1.88 (m, 2H), 1.23 (s, 6H).

EXAMPLE 7

Preparation of Comparative Compound A

Comparative compound A corresponds to compound 1 of patent application WO 2006/122 680 and was prepared as described in the said patent application.

EXAMPLE 8

Preparation of Comparative Compound B

Comparative compound B corresponds to compound 6 of patent application WO 2007/014 687 and was prepared as described in the said patent application.

EXAMPLE 9

Preparation of Comparative Compound C

Comparative compound C corresponds to compound 13 of patent application WO 2007/014 687 and was prepared as described in the said patent application.

EXAMPLE 10

Test of in vitro Activity

This test allows evaluation of the inhibitory capacity on the production of the PGE$_2$ and the selectivity relative to the production of the PGF$_{2\alpha}$.

The cell line A549, human pulmonary adenocarcinoma, was used, which is particularly sensitive to stimulation with pro-inflammatory cytokines, for instance IL-1$_\beta$, and, in response to this stimulation, is particularly active in the production and release of two prostanoids: PGE$_2$ and PGF$_{2\alpha}$ (Thoren S. Jakobsson P-J, 2000).

The cells were stimulated with IL-1$_\beta$ (1 ng/ml) and simultaneously treated with the test compound for 22 hours in an appropriate culture medium (DMEM—Dulbecco's Modified Eagle's Medium) supplemented with 5% foetal calf serum and L-glutamine (4 mM final) in an incubator at 37° C. and at a CO$_2$ concentration of 5%.

After the incubation, the amount of PGE$_2$ and PGF$_{2\alpha}$ produced and released into the supernatant were assayed using an EIA kit (produced and sold by Cayman Chemicals, Ann Arbor, Mich., USA).

The comparative compound used was indomethacin at a concentration of 10 nM (Sigma-Aldrich), a non-steroidal anti-inflammatory drug that inhibits in equal measure both PGE$_2$ and PGF$_{2\alpha}$.

The results, expressed as the IC$_{50}$ values, i.e. as the concentration of compound that inhibits 50% of the production of PGE$_2$ and of PGF$_{2\alpha}$ relative to the cells that have been stimulated, but not treated with the same compound, are given in Table 2. The inactivity or the reduced activity of the compound on the biosynthesis of PGF$_{2\alpha}$ is an indication of selectivity towards the production of PGE$_2$ and thus of selective inhibition of mPGES-1.

TABLE 2

|  | IC$_{50}$ [μM] | |
|---|---|---|
| Compound | PGE$_2$ | PGF$_{2\alpha}$ |
| 1 | 2.9 | >100 |
| 2 | 2.3 | >100 |
| 3 | 1.4 | >100 |
| 4 | 5.6 | >100 |
| 6 | 0.6 | >100 |
| Indomethacin | 0.005 | 0.003 |

EXAMPLE 11

Test of in vivo Activity

The test compound was evaluated in the model of acetic acid-induced writhing in mice (Stock J. L. et al., J. Clin. Inv. 2001, 107: 325-331). This test allows evaluation of the antinociceptive activity of the compounds of the invention in a model of inflammatory pain.

Female CD-1 mice weighing 25-30 g were used for the test. The animals were treated intraperitoneally with the test compound (0.1-10 mg/kg) suspended in methylcellulose (MTC). The control animals were treated with the vehicle alone (MTC) via the same route.

Half an hour after the treatment, an intraperitoneal injection of acetic acid (0.7% v/v in physiological saline, 16 μl/g of body weight) was given to the animals to induce inflammatory pain and to check the effects of the test compound on the nociceptive response.

Immediately after the administration of acetic acid and for the following 20 minutes the number of writhes was measured, which represents the parameter for evaluation of the nociceptive response.

As shown in Table 3, the compound of the invention induced in a dose-dependent manner a reduction in the number of writhes in the 20 minutes following the administration of acetic acid, compared with the animals treated with MTC alone.

TABLE 3

| Treatment | Dose (mg/kg) | No. of writhes | % of inhibition |
|---|---|---|---|
| Vehicle | — | 48.4 ± 3.66 | — |
| Compound 1 | 0.1 | 38.4 ± 3.99 | 21 |
|  | 1 | 31.5 ± 5.72 | 35 |
|  | 10 | 12.8 ± 2.46 | 74 |

EXAMPLE 12

Test of Metabolic Stability in Human and Rat Hepatic Microsomes

This test allows evaluation of the metabolic stability of the compounds of the invention and of the comparative compounds in rats and in man.

The test compounds were incubated in human hepatic microsomes (donor pool, Xenotech) and in hepatic microsomes from Sprague-Dawley rats (donor pool, Xenotech) and the comparison of the test compound was measured so as to have an estimate of the metabolic stability in various species using HPLC/MS/MS with an Applied Biosystems 4000 QTrap mass spectrometer.

The compounds to be analysed, at a final concentration of 0 and 1 µM, were placed in a suspension containing the pool of microsomes at a final concentration of 0.5 mg/mL in a final volume of 200 µL, in 96-well plates. The test was standardized with phosphate buffer (75 mM, pH 7.4) and with the NADPH regenerating system ($MgCl_2$: 3.3 mM; G6P: 3.3 mM; G6PD: 0.4 U/mL; NADP+: 1.3 mM). The reference compounds warfarin, propranolol and testosterone (Sigma) were incubated as a cocktail and treated as for the test compounds. The samples were incubated at 37° C. in a humidified incubator. At time 0 and after 60 minutes, 100 µL of acetonitrile containing the internal standard (0.2 µM of metoprolol and 0.4 µM of diclofenac) were added to stop the reaction.

The samples were centrifuged before analysis. The HPLC/MS/MS analysis was performed using an electrospray ion source in positive ionization and SRM (Single Reaction Mode). The chromatographic conditions entail the use of an XDB-C18 column (2.1×50 mm, Agilent) and a gradient from 5% to 91% of acetonitrile in water containing 0.1% formic acid (total runtime equal to 6 minutes); the flow rate was 0.5 ml/minute.

The areas of the peaks for the test compounds were integrated and the results expressed as the analyte area/internal standard (PAR) area ratio. For each time, two samples were analysed and the mean value calculated. The percentage of the value of remaining compound was calculated as:

% unmetabolized compound=100*(mean $PAR_{Tfinal}$/mean $PAR_{T0}$).

The results for compounds 1 to 6 are given in Table 4, together with the results for the comparative compounds A, B and C and for the reference compounds. The compounds of the present invention showed improved metabolic stability relative to the comparative compounds.

TABLE 4

| Compound | Rat | Man |
|---|---|---|
| 1 | 58% | 81% |
| 2 | 68% | 82% |
| 3 | 65% | 77% |
| 4 | 58% | 7% |
| 5 | 63% | 76% |
| 6 | 74% | 65% |
| A | 0.2% | 51% |
| B | 0.4% | 55% |
| C | 4.0% | 22% |
| Warfarin | 97% | 103% |
| Propranolol | 0.4% | 66% |
| Testosterone | 0% | 27% |

EXAMPLE 13

Test of in vitro Absorption

This test allows evaluation of the amount absorbed by the intestinal barrier of the compounds of the invention and of the comparative compounds using the Caco-2 cell line as an in vitro model of intestinal barrier. The permeability test on Caco-2 cells represents an in vitro system approved for predicting and estimating the in vivo intestinal absorption of a drug. When the Caco-2 cells are cultured on a porous filter for about 21 days, they have the capacity to differentiate into enterocytes. In practice, during this period, the Caco-2 cells undergo spontaneous morphological and biochemical changes that result in the formation of a polarized cellular monolayer which has on the apical surface a well-defined "brush border" and form "tight junctions" between the cells, thus representing a suitable model for analysis of the intestinal permeability of drugs.

The following materials were used to perform the test:
Lucifer yellow (Sigma)
Hank's balanced saline solution (HBSS) (Invitrogen)
radioactive reference standard (Perkin Elmer)
Caco-2 cells (ATCC)
Caco-2 MultiScreen™ plates (Millipore)
HPLC/MS/MS with Applied Biosystems 4000 QTrap mass spectrometer
Acetonitrile containing 0.2 µM of metoprolol as internal standard.

The compounds undergoing the test were diluted from a 10 mM stock solution in HBSS to a final concentration of 10 µM. The system consisted of a confluent cellular monolayer in culture for 21-28 days. The reference compounds (Lucifer yellow, atenolol, propranolol and digoxin) were included in each test as quality controls and for comparison with the compounds undergoing the test.

Each compound was tested in triplicate, bidirectionally, at pH 7.4, from the apical to the basolateral compartment (A→B) and from the basolateral to the apical compartment (B→A).

The samples collected at the given time were analysed by HPLC-MS/MS, using an electrospray ion source in positive ionization and SRM (Single Reaction Mode). The chromatographic conditions entailed the use of an XDB-C18 column (2.1×50 mm, Agilent) with a gradient from 5% to 91% of acetonitrile in water containing 0.1% formic acid (total runtime equal to 6.5 minutes) and a flow rate of 0.5 ml/minute. Metoprolol was used as the internal standard.

The concentration data were used to calculate the apparent permeability values ($P_{app}$), and the mean and standard deviation of the $P_{app}$ were calculated.

The flux ratio was calculated as $P_{app}(B{\rightarrow}A)/P_{app}(A{\rightarrow}B)$. The recovery percentage was calculated as:

(amount in the receiving compartment+amount in the donor compartment)/nominal amount The area of the peaks of the test compounds were integrated and the results were expressed as the analyte area/internal standard area ratio and corrected for the dilution factor used during the preparation of the sample. The apparent permeability coefficients were calculated using the following equation:

$$P_{app} = \left(\frac{V_A}{Area \times Time}\right) \times \left(\frac{[product]_{receiving}}{[product]_{donor}}\right)$$

in which:
$V_A$ volume in the receiving well (0.25 mL for the test from A→B, 0.075 mL for the test from B→A)
Area area of the membrane surface (0.11 cm²)
Time total transport time (3600 seconds)
The values obtained were classified on the basis of the following evaluation criterion.
Low $P_{app} < 2 \times 10^{-6}$ cm/sec
Medium $2 \times 10^{-6}$ cm/sec $< P_{app} < 20 \times 10^{-6}$ cm/sec
High $P_{app} > 20 \times 10^{-6}$ cm/sec
The results for compounds 1 to 6 are given in Table 4, together with the results for the comparative compounds A, B and C and for the reference compounds. The compounds of the present invention showed improved expectation of absorption relative to the comparative compounds.

TABLE 5

| Compound | Absorption |
| --- | --- |
| 1 | High |
| 2 | High |
| 3 | High |
| 4 | High |
| 5 | High |
| 6 | High |
| A | Low |
| B | Low |
| C | Medium |
| Lucifer yellow | Low |
| Atenolol | Low |
| Propranolol | High |
| Digoxin | Low |

EXAMPLE 14

Test of in vivo Bioavailability

This test allowed evaluation of the in vivo bioavailability of the compounds of the invention, thus making it possible to evaluate and compare the pharmacokinetic profile of the test compounds.

The tests were performed using the cassette method, i.e. by administering orally several products simultaneously to the same animal, at a dose of 5 mg/kg. The products were suspended in methylcellulose (MTC). The treated animals were catheterized for the serial collection of blood samples performed by means of an automatic sampling system. The plasmatic concentrations of the products were measured by HPLC/MS/MS. The profiles of the plasmatic concentrations over time made it possible to evaluate the relative bioavailability of the test products in terms of rate ($t_{max}$ and $C_{max}$) and species (AUC). The slope of the curve in the end portion also allowed a comparative evaluation of the rate of elimination of the compounds from the plasma, the slower the rate, the lower the slope. Three animals were treated for each combination of compounds. The compound that had a higher $C_{max}$ and AUC and an expected $t_{max}$ relative to the others was selected since it showed a good rate of in vivo absorption.

The comparative product used was compound C, which showed limited absorption, whereas compounds 1, 2 and 3 of the present invention showed good bioavailability characteristics.

The results, expressed as the $C_{max}$, i.e. as the maximum concentration of drug reached in the plasma, $T_{max}$, i.e. the time required to reach the maximum drug concentration in the plasma, and $AUC_{0-7}$, i.e. the area under the curve of the plasmatic concentrations of drug over time, measured in the first seven hours after administration, are given in Table 5.

TABLE 5

| Compound | $C_{max}$ ng/ml | $T_{max}$ h | $AUC_{0-7}$ ng/ml*h |
| --- | --- | --- | --- |
| 1 | 1200 | 1.5 | 5754 |
| 2 | 984 | 4.3 | 5403 |
| 3 | 457 | 1.8 | 2668 |
| C | 165 | 1.7 | 751 |

The invention claimed is:
1. A 3-aminocarbazole compound, represented by formula (I):

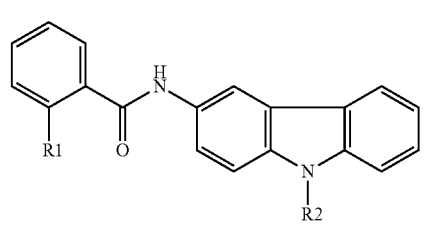

wherein
R1 is a halogen atom, a methyl group, a trihalomethyl group, a nitro group, a cyano group or a triflate group, and
R2 is a linear or branched carbonylalkyl group having from 1 to 8 carbon atoms, or
a pharmaceutically acceptable salt thereof, a polymorphic crystal form thereof, a stereoisomer thereof, an enantiomer thereof, or a prodrug thereof.

2. A 3-Aminocarbazole compound, pharmaceutically acceptable salt, polymorphic crystal form, stereoisomer, enantiomer, or a prodrug according to claim 1, where R1 is a fluorine or chlorine atom, or a trifluoromethyl or trichloromethyl group, and R2 is a linear or branched carbonylalkyl group having from 1 to 4 carbon atoms.

3. A 3-aminocarbazole compound, represented by formula (I):

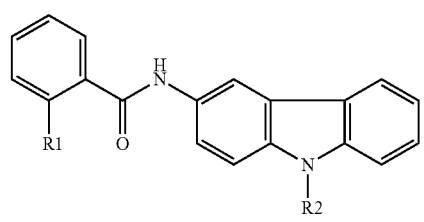

wherein
R1 is trifluoromethyl, and
R2 is —CH₂COCH₃, or
a pharmaceutically acceptable salt thereof, a polymorphic crystal form thereof, a stereoisomer thereof, an enantiomer thereof, or a prodrug thereof.

* * * * *